(12) United States Patent
Nakamura (10) Patent No.: US 6,855,685 B2
(45) Date of Patent: Feb. 15, 2005

(54) ANTI-CANCER AGENT

(76) Inventor: Toshikazu Nakamura, 4-1, Takamidai, Takatsuki-shi, Osaka 569-1020 (JP)

( * ) Notice: Subject to any disclaimer, the term of this patent is extended or adjusted under 35 U.S.C. 154(b) by 29 days.

(21) Appl. No.: 09/951,629

(22) Filed: Sep. 14, 2001

(65) Prior Publication Data

US 2002/0004480 A1 Jan. 10, 2002

Related U.S. Application Data

(63) Continuation of application No. 09/471,032, filed on Dec. 23, 1999, now abandoned, which is a continuation of application No. 09/051,968, filed as application No. PCT/JP96/03105 on Oct. 23, 1996, now abandoned.

(30) Foreign Application Priority Data

Oct. 24, 1995 (JP) ............................................. 7-300728

(51) Int. Cl.$^7$ ........................ A01N 37/18; A61K 39/00; A61K 38/00; C07K 17/00
(52) U.S. Cl. ........................ 514/2; 424/198.1; 514/12; 530/395
(58) Field of Search ...................... 514/12, 2; 530/395; 424/198.1

(56) References Cited

FOREIGN PATENT DOCUMENTS

| EP | 0550296 A | * | 7/1993 |
|---|---|---|---|
| JP | 625010 | | 2/1994 |
| WO | 9205184 | | 4/1992 |
| WO | 9323541 | | 11/1993 |
| WO | 9406909 | | 3/1994 |
| WO | WO 96 40914 | | 12/1996 |

OTHER PUBLICATIONS

Bardelli A et al J. Biotechnol Sep. 1994;37(2):109–122.*
Coffer A et al Biochem J. Aug. 1991;278(Pt1):35–41.*
Nakamura T et al Nature Nov. 1989;342(6248):440–443.*
Nakamura T et al FEBS Lett Nov. 1987;224(2):311–316.*
Nakamura et al., FEBS Letters, vol. 224, No, 2, pp. 311–316, Nov. 1987, Elsevier Science.
Nakamura et al., Nature, vol. 342, No. 6248, pp. 440–443, Nov. 23, 2989.
Bardelli et al., Journal of Biotechnology, vol. 37, pp. 109–122, Elsevier Science.
Coffer et al., Biochem. J., vol. 278, pp. 35–41, 1991.

Date et al., FEBS Letters, vol. 420, pp. 1–6, 1997.
Chan, et al; Science, vol. 254, Nov. 1991, pp. 1382–1385.
Lokker and Godowski; Journal of Biological Chemistry, vol. 268, No. 23, Aug. 15, 1993, pp. 17145–17150.
Tashiro, et al; Proc. Natl. Acad. Sci. USA: vol. 87, Apr. 1990, pp. 3200–3204.
Nakamura, et al., Letters to Nature; vol. 342; Nov. 23, 1989; pp. 440–443.
Lomri, et al., FEBS Letters; vol. 222, No. 2, Oct. 1987; pp. 311–316.
Nakamura, et al; Proc. Natl. Acad. Sci USA ; vol. 83, Sep. 1986; pp. 6489–6493.
Nakamura, et al; Biochemical and Biophysical Research Communications; vol. 122, No. 3, Aug. 16, 1984; pp. 1450–1459.
Shimura, et al: Jpn. J. Cancer Res.; vol. 86 Jul. 1995; pp. 662–669.
Naldini, et al; Oncogene, vol. 6, 1991, pp. 501–504.
Bottaro, et al; Science, vol. 251, Feb. 15, 1991; pp. 802–804.
Nakamura, T.; Progress in Growth Factor Research, vol. 3, 1991, pp. 67–85.
Matsumoto, et al; Journal of Biological Chemistry, vol. 269, No. 50, Dec. 16, 1994; pp. 31807–31813.
Bellusci, et al; Oncogene, vol. 9, 1994, pp. 1091–1099.
Rahimi, et al; DNA and Cell Biology, vol. 13, No. 12, 1994; pp. 1189–1197.
Seslar, et al; Cancer Research; vol. 53, Mar. 15, 1993; pp. 1233–1238.
Jiang, et al.; Clin. Exp. Metastasis, vol. 11, 1993, pp. 235–242.
Rygaard, et al; Intern. J. Oncology, vol. 2, 1993, pp. 991–996.
Nakamura and Matsumoto; Gann Monograph on Cancer Research, No. 42, pp. 92–112.

* cited by examiner

Primary Examiner—Gary Nickol
Assistant Examiner—Christopher Yaen
(74) Attorney, Agent, or Firm—Birch, Stewart, Kolasch & Birch, LLP (57) ABSTRACT

The invention relates to an anti-cancer agent containing α-chain protein (α-fragment) of HGF (hepatocyte growth factor) as an active ingredient. The active ingredient of α-fragment has a specific suppressing effect on invasion and metastasis of cancer cells such as gallbladder cancer, lung cancer and other, which are highly metastatic and result in a high mortality. Therefore, the agent of the invention is used in treatment and prevention of cancer as an anti-cancer agent, and is extremely useful clinically.

5 Claims, 8 Drawing Sheets

ANTI-CANCER AGENT

This application is a continuation of application Ser. No. 09/471,032, filed on Dec. 23, 1999 now abandoned, which is a continuation of Ser. No. 09/051,968 filed on Apr. 24, 1998 now abandoned, for which priority is claimed under 35 U.S.C. §120. Application Ser. No. 09/051,968 is the national phase of PCT International Application No. PCT/JP96/03105 filed on Oct. 23, 1996 under 35 U.S.C. §371. The entire contents of each of the above-identified applications are hereby incorporated by reference.

TECHNICAL FIELD

The present invention relates to an anti-cancer agent. More specifically, it relates to a novel anti-cancer agent containing α-chain of HGF (hepatocyte growth factor) as an active ingredient, capable of suppressing carcinoma, especially invasion and metastasis of carcinoma, on the basis of its c-Met/HGF receptor-antagonist activity.

BACKGROUND ART

Control of cancer is a most important subject in today's medicine, and new cancer therapy and new anti-cancer agents are topics of the greatest interest among medical and pharmaceutical researchers. At the present time, the number one cause of death in Japan is cancer, and many new patients are found every year.

As anti-cancer agents used in chemotherapy, aside from the conventional alkylating agents, metabolic antagonists, and antibiotics, microorganism-derived bioreactive modification substances represented by PICIBANIL (trade name of Chugai Pharmaceutical, Japan) and KRESTIN (trade name of Sankyo Pharmaceutical, Japan) once flourished. Existing compounds such as alkylating agents originally made use of cytotoxicity, and the uses were considerably limited owing to manifest side effects, but PICIBANIL and other later bioreactive modification substances have actions of enhancing the immune function of the body and expel cancer cells. However, as their limits have come to be known, attention has been turned to bio-active proteins derived from higher animals such as interferon, interleukin 2, and TNF (tumor necrosis factor). Yet, their action spectra were actually by far broader than initially estimated, and the belief that they were free from side effects were lost.

In this background, it is at least true that the treatment of cancer is changing its direction, that is, from the conventional evaluation of mere fighting against the cancer focus to the concept considering "quality of life" to evaluate the treatment in the process of improvement of total function of the body, and HGF discovered by the present inventor has been already reported that it is an active ingredient for anti-cancer agent (Japanese Laid-open Patent No. 6-25010).

As mentioned above, the existing anti-cancer agents are far from a decisive remedy in consideration of the side effects and doubts about the anti-cancer action itself, and the bio-active proteins of the next generation are mainly factors relating to the immune system as far as developed in the past, and are not always expected to be used widely as ultimate anti-cancer agents. Accordingly, among the bio-active proteins produced in the body, in particular, among those definite in physiological action and researched sufficiently of the spectrum of activity, it is required to discover a true anti-cancer agent. Especially, since the bio-active proteins, interferons and interleukins developed so far are mostly factors relating to the immune system, biological factors having a completely different action seems to be important as a future anti-cancer agent.

In Japan, cancer is the number one cause of death as mentioned above, but it may be dared to say that its risk depends on invasion and metastasis of cancer cells. Several growth factors have been reported to be related to the ability of invasion and metastasis of cancer cells, and recently HGF has been disclosed to be a strong factor for inducing invasion and metastasis ability to various cancer cells (H. Shimura et al., J. Jap. Cancer Res. 86, 662–669). Actually, the invasion ability of lung cancer and gallbladder cancer known to be extremely high in malignancy has been confirmed to be induced depending on HGF, and HGF level in the primary tissues of lung cancer is known to be a risk factor closely (correlating) correlated with the malignancy and mortality of lung cancer.

HGF is a protein which has been discovered as a factor for proliferating liver parenchymal cells in vitro (Biochem Biophys Res Commun, 122, 1450, 1984; Proc. Natl. Acad. Sci. USA, 83, 6489, 1986; FEBS Letter, 22, 311, 1987; Nature, 342, 440, 1989; Proc. Natl. Acad. Sci. USA, 87, 3200, 1990). This HGF first discovered as a factor for specifically proliferating liver parenchymal cells has been shown to have various activities in the body such as tissue wound healing as a result of recent studies by the present inventor and many other researchers, and it is highly expected to be applied into remedies in humans and animals, as well as the subject of study. Concerning a receptor of such HGF, the recent studies unveiled that the c-Met proto oncogene codes HGF receptor (Bottaro et al., Science, 251, 802–804, 1991; Naldini et al., Oncogene, 6, 501–504, 1991).

It is thus clarified that HGF is a factor for powerfully inducing invasion and metastasis ability to various cancer cells, and development of antagonist and inhibitor for specifically blocking the invasion and metastasis ability of cancer cells by HGF seems to be an extremely important subject of study from the viewpoint of control of cancer

DISCLOSURE OF THE INVENTION

As a result of intensive studies from such viewpoint, the inventor discovered a substance having an activity for suppressing the invasion and metastasis ability of cancer cells induced by HGF (that is, the antagonist activity to the c-Met/HGF receptor of cells), and found that this substance suppresses the invasion and metastasis ability of cancer cells and is hence extremely useful as an anti-cancer agent, and thereby completed the present invention. It is therefore an object of the invention to present an extremely useful medicine as an anti-cancer agent on the basis of the antagonist activity of c-Met/HGF receptor of cells.

That is, the invention provides an anti-cancer agent containing a protein having the following physicochemical properties and physiological activities (hereinafter referred to as α-fragment) as an active ingredient:

a) composed of α-chain of HGF;

b) having molecular weight of about 55–69 kDa; and c) having antagonist activity of c-Met/HGF receptor.

Other inventions of the present invention relate to a method of treatment for cancer by administering an effective amount of α-fragment to humans or mammals; and a use of α-fragment for manufacturing the anti-cancer agent.

BEST MODE OF CARRYING OUT THE INVENTION

As mentioned above, the inventor has been studying growth factors of liver parenchymal cells for years, and has succeeded in isolation and purification of HGF. Initially, HGF is a polypeptide discovered to be a factor for promoting proliferation of live parenchymal cells, and it is discovered by the inventor that it functions also as motogen for promoting cell motility, in addition to the function of cell growth control (T. Nakamura, Prog. Growth Factor Res., 3, 67–85, 1991). Promotion of cell motility by HGF is related with decrease of adhesion between cells through cadherin by phosphorylation of β-catenin, and information transmitting system through activation of rho small G protein. More recently, it has been disclosed that p125FAK (focal adhesion kinase) is positioned downstream of rho, so that transient phosphorylation of p125FAK is caused by HGF (K. Matsumoto et al., J., Biol. Chem. 269, 31807–31813, 1994). After stimulation of HGF, phosphorylation of p125FAK contributes to initial formation of focal adhesion and reconstruction of cell skeleton, and in promotion of cell motility by HGF, it is considered that the interaction of cells and matrix is regulated through the p125FAK.

It has been traditionally known that the proliferation and invasion and metastasis ability of cancer cells depend much on the interaction of cancer cells and surrounding stromal cells (tumor-host relationship). The inventor unveiled that HGF derived from the host interstitium and HGF-inducing factor derived from cancer cells (injulin) contribute to aggravation of cancer (proliferation, invasion and metastasis) (K. Matsumoto et al., Gann Monograph No. 42: Growth Factors: Cell growth, Morphogenesis and Transformation, CRC press 92–112, 1994; K. Rygaard et al., Intern. J. Oncology, 2, 991–996, 1993; W. G. Jiang et al., Clin. & Exp. Metastasis, 11, 235–242, 1993; S. P. Seslar et al., Cancer Res., 58, 1233–1238, 1993; N. Rahimi et al., DNA and Cell Biol., 13, 1189–1197, 1994; S. Bellusci et al., Oncogene, 9, 1091–1099, 1994).

Gallbladder cancer is generally a malignant cancer high in metastasis rate and mortality rate. Human gallbladder cancer cells show a high invasion in the stromal cells of the host, but will not invade into the gel in the culture on collagen gel in vitro. However, in co-cultivation between the normal stromal fibroblast and collagen gel, gallbladder cancer cells actively invade into the gel, and the invasion ability of gallbladder cells is induced by the interaction with the stromal cells through a liquid factor. Moreover, invasion of cancer cells in the co-cultivation is completely inhibited by the addition of anti-HGF antibody, and the stromal-derived invasion factor is found to be HGF. This invasion of gallbladder cancer cells into the gel is not induced by representative growth factors such as EGF, TFG-β, PDGF and bFGF, and it is specific to HGF. On the other hand, gallbladder cancer cells produce and secrete factors for inducing HGF production of stromal fibroblast, and the substance of this HGF inducer was found to be IL-1β. The substance of the stromal-derived invasion factor not only in the human gallbladder cancer cells, but also in cells of many carcinomata such as oral mucosal epithelial cancer cells is found to be HGF (K. Rygaard et al., Intern. J. Oncology, 2, 991–996, 1993; W. G. Jiang et al., Clin. & Exp. Metastasis, 11, 235–242, 1993; S. P. Seslar et al., Cancer Res., 58, 1233–1238, 1993; N. Rahimi et al., DNA and Cell Biol., 13, 1189–1197, 1994).

It is said that the mortality by cancer can be decreased by preventing invasion and metastasis of cancer cells. More than 80% of cancer is carcinoma, and most of them are HGF-target cells expressing c-Met/HGF receptor. It is hence important to develop an antagonist for blocking the invasion and metastasis function of cancer cells caused by HGF.

The inventor disclosed the following points in the sequential studies on HGF. First of all, HGF is a heterodimer comprising about 69 kDa of α-chain and about 34 of β-chain. The α-chain of HGF contains a hairpin domain at N-terminal and four Kringle domains, and the β-chain contains a serine protease-like domain, and hence HGF is a growth factor having a very unique domain structure. The inventor already prepared various deletion-type HGFs eliminated domain structures in the HGF molecule by gene engineering techniques, and disclosed that the N-terminal hairpin and first and second Kringle domains in the a-chain are a minimum domain binding to c-Met/HGF receptor. Therefore, by genetically introducing the mutation into this minimum receptor binding domain. It is considered possible to manufacture a HGF receptor-antagonist. Hitherto, in studies of factors for suppressing invasion and metastasis of cancer cells, the target was mainly the matrix protease derived from cancer cells, but an effective substance for blocking invasion and metastasis of cancer cells has not been unveiled yet.

By contrast, the object of the invention is to block the signal for inducing invasion and metastasis of cancer cells at the upstream side, and it is a major feature that it is based on a completely new strategy, and this is a pioneering invention.

The anti-cancer agent of the invention contains the protein (α-fragment) having the above-mentioned physicochemical properties and physiological activities as an active ingredient, and this protein can be obtained, for example, by a method of decomposing HGF enzymatically, a method of preparing by gene engineering technique, a method of preparing chemically and the like.

As to HGF used in the enzymatic decomposition method, HGF prepared by various methods may be used. Many methods are known to prepare HGF, and, for example, HGF can be obtained by extraction and purification from organs such as liver, spleen, lung, bone marrow, brain, kidney, placenta and the like, blood cells such as platelets, leukocytes and the like, plasma and serum of mammals such as rat, cow, horse, sheep and the like (FEBS Letters, 224, 312, 1987; Proc. Acad. Sci. USA, 86, 5844, 1989, etc.).

Also, it is possible to obtain HGF by cultivation of primary culture cells or cell lines producing HGF, followed by separation and purification from the culture product (e.g. culture supernatant, cultured cell, etc.). Further, HGF can be obtained by gene engineering method which comprises recombining the gene coding HGF with a proper vector, inserting it into a proper host cell to give a transformant, and separating the desired recombinant HGF from the culture supernatant of the transformant (e.g. Nature, 342, 440, 1989, Japanese Patent Kokai Nos. 111383/1993 and 255096/1991, Biochem. Biophys. Res. Commun., 163, 967, 1989).

The host cell is not specifically limited, and various host cells conventionally used in gene engineering methods can be used, which are, for example, *Escherichia coli, Bacillus subtilis*, yeast, filamentous fungi, and plant or animal cells.

More specifically, the method of extracting and purifying HGF from live tissues is, for example, to administer carbon tetrachloride to a rat intraperitoneally, remove a liver from the rat with hepatitis, grind it, and purify it by an ordinary protein purifying technique such as gel column chromatography using S-Sepharose and heparin Sepharose, HPLC and the like.

Further, by the gene engineering method, animals cells such as Chinese hamster ovary (CHO) cells, mouse C127 cells, monkey COS cells, Sf (*Spodoptera frugiperda*) cells and the like are transformed with the gene coding the amino acid sequence of HGF, and HGF can be obtained from the culture supernatant of the transformants. Incidentally, HGF derived from either humans or mammals can be used, but HGF derived from humans are preferred, and human recombinant HGF (Japanese Patent Kokai No. 111383/1993) is more preferable.

As to HGF thus obtained, as far as substantially effective as HGF, there are possibilities that a part of the amino acid sequence will be deleted or substituted with other amino acid(s), that another amino acid sequence is partially inserted, that 1, 2 or more amino acids are attached to the C and/or N terminals, or that sugars are similarly deleted or substituted.

Enzymatic decomposition of HGF is carried out by, for example, digesting HGF by using enzyme such as elastase and the like. Successively, the digested product is purified by a conventional protein purification method such as high performance liquid chromatography and the like, and a low molecular HGF composed of about 55–69 kDa fragment containing α-chain is isolated, so that the protein (α-fragment) having the above-mentioned physiocochemical properties and physiological activities is obtained.

α-fragment of the invention is not limited to those obtained by the above methods alone, but may be prepared chemically according to the conventional peptide synthesis method. Also, α-fragment can be obtained by the gene engineering method mentioned above by using genes coding the amino acid sequence of α-fragment.

As shown in Examples below, α-fragment is disclosed to have the antagonist activity of c-Met/HGF receptor for blocking the mitogen and motogen activity of HGF, and suppress the invasion of cancer cells. Therefore, the agent of the invention mainly composed of α-fragment is useful as the anti-cancer agent for humans and mammals (for example, cow, horse, pig, sheep, monkey, dog, cat, etc.), especially as invasion suppressant and metastasis suppressant of cancer cells.

Other inventions of the present invention relate to the method of treatment for cancer by administering an effective amount of this α-fragment to humans and mammals (for example, cow, horse, pig, sheep, monkey, dog, cat, etc.); and to the use of α-fragment for manufacturing the anti-cancer agent.

The anti-cancer agent of the invention is prepared in various dosage forms (for example, liquid, solid, capsule, etc.), and it is generally prepared as an injection of the active ingredient of α-fragment only, or together with a conventional carrier, or as an oral preparation together with a conventional carrier. The injection may be prepared by a conventional method, for example, α-fragment is dissolved in a proper solvent (for example, sterilized water, buffer solution, physiological saline, etc.), filtered to be sterilized, and is contained in an aseptic container. The content of α-fragment in the injection is adjusted usually to about 0.0002 to 0.2 (w/v %), or preferably about 0.001 to 0.1 (w/v %). As the oral preparation, it is prepared into, for example, tablet, granule, fine granule, powder, soft or hard capsule, liquid, emulsion, suspension, syrup, etc., and such dosage forms may be prepared by the conventional manufacturing methods. The content of α-fragment in the preparation may be properly adjusted according to the dosage form, the applicable diseases, etc.

In pharmaceutical manufacture, preferably, a stabilizing agent may be added, and examples of such stabilizing agent may include, among others, albumin, globulin, gelatin, mannitol, glucose, dextran, and ethylene glycol. The preparation of the invention may also contain other additives necessary for manufacture, such as excipient, dissolving aid, antioxidant, pain-alleviating agent, isotonic agent and the like. In liquid preparation, it is preferred to store it under frozen conditions or after the removal of water by a process such as freeze-drying. The freeze-dried preparation is used by dissolving again by adding distilled water for injection and the like before use.

The preparation of the invention is administered through a proper route according to the dosage form. For example, the injection can be administered intravenous, intraartery, subcutaneous, intramuscular and the like. The dose is properly adjusted depending on the symptom, agent, or body weight of the patient, and usually 0.01 mg to 100 mg of α-fragment is used, which is administered once a day or in several divided portions.

INDUSTRIAL APPLICABILITY

In the invention, the active ingredient of α-fragment has a specific effect to suppress invasion or metastasis of cancer cells such as gallbladder cancer, lung cancer and others, which are highly metastatic and result in a high lethality. Therefore, the anti-cancer agent and therapeutic method of the invention may be used in treatment and prevention of cancer, and are extremely useful clinically.

EXAMPLES

The invention is more specifically described below by referring to Examples and Test Examples, but the invention is not limited to them alone.

Figure 1:
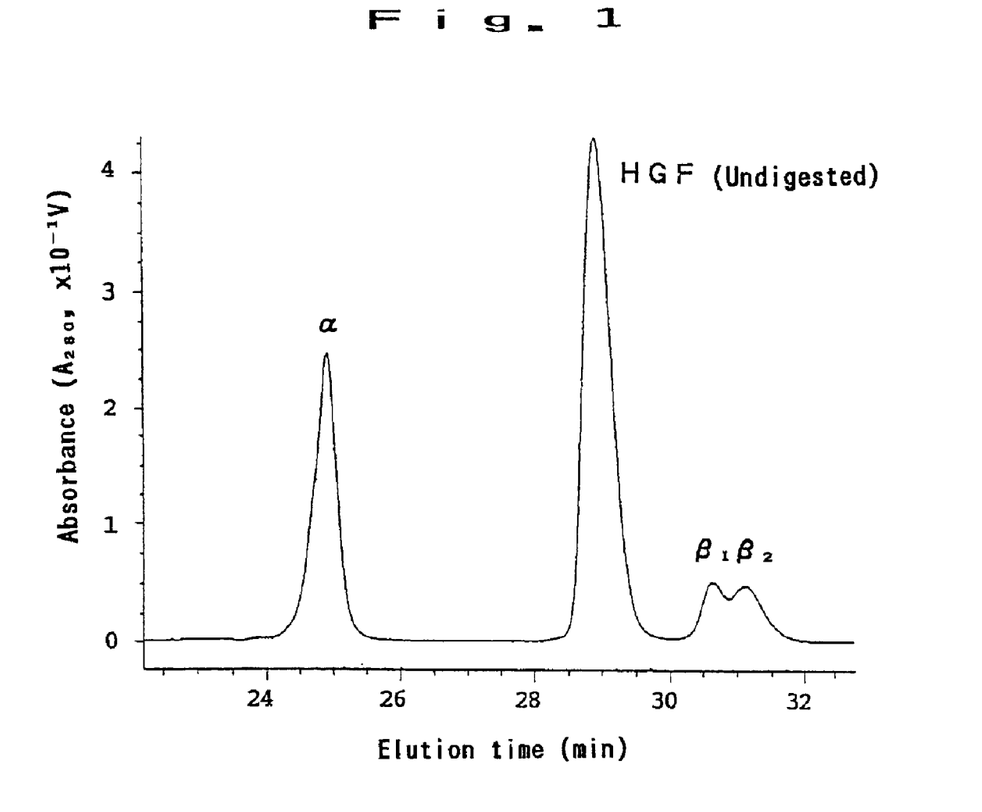
FIG. 1 is a chromatogram obtained when enzyme-digested HGF is purified by reverse-phase HPLC.
Figure 2:
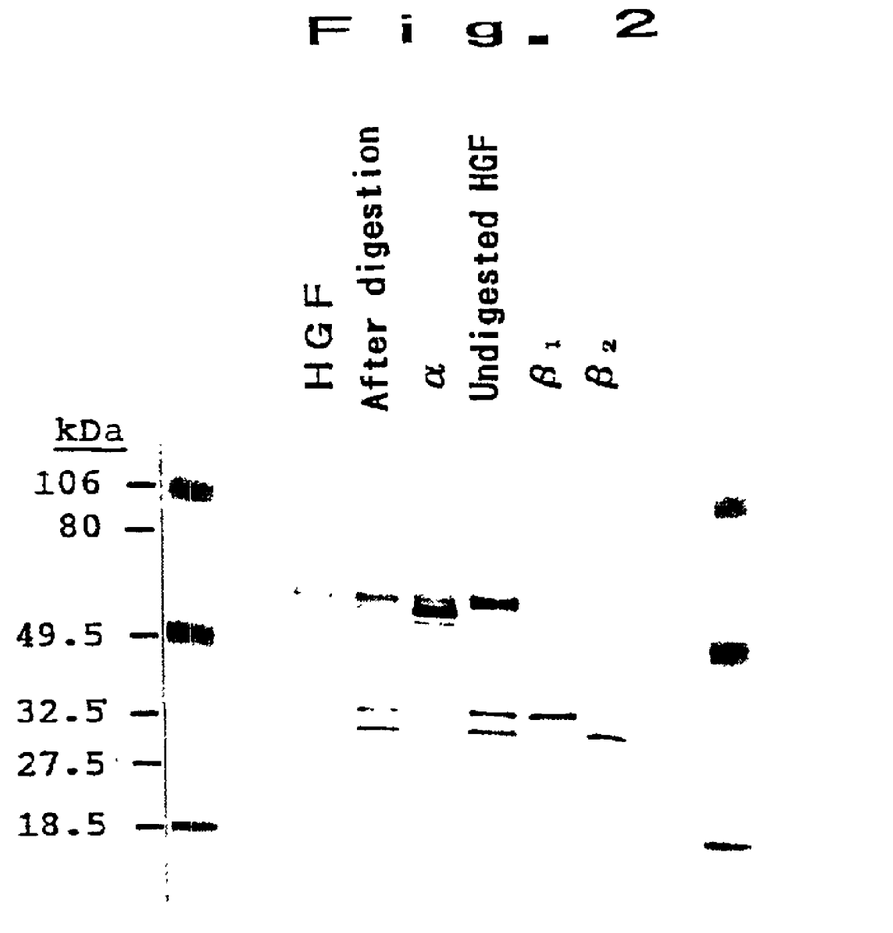
FIG. 2 is a photograph of electrophoresis showing the result of electrophoresis (SDS-PAGE, in reducing condition) of enzyme-digested HGF purified by reverse-phase HPLC.

Example 1
Isolation and Refining of α-Fragment of HGF 900 mg of recombinant HGF was digested in elastase for 1 hour, and it was purified in reverse-phase HPLC (C4). Its chromatogram is shown in FIG. 1. As shown in FIG. 1, four peaks were obtained, and the first peak was identified to be α-fragment, the second peak to be undigested HGF, and third and fourth peaks to be β-1 and β-2, respectively. Further, by a freeze-drying system, the solvent was removed, and each of the fractions was collected and suspended again in distilled water. The obtained substances were found to be α and β-fragments by SDS-PAGE (see FIG. 2). The amino acid sequence of the α-fragment is shown by SEQ ID NO:1. As a result of determination of protein, 178 mg of α-fragment was obtained.

Example 2
Analysis of Action of Motogen using MDCK Cells

Figure 3:
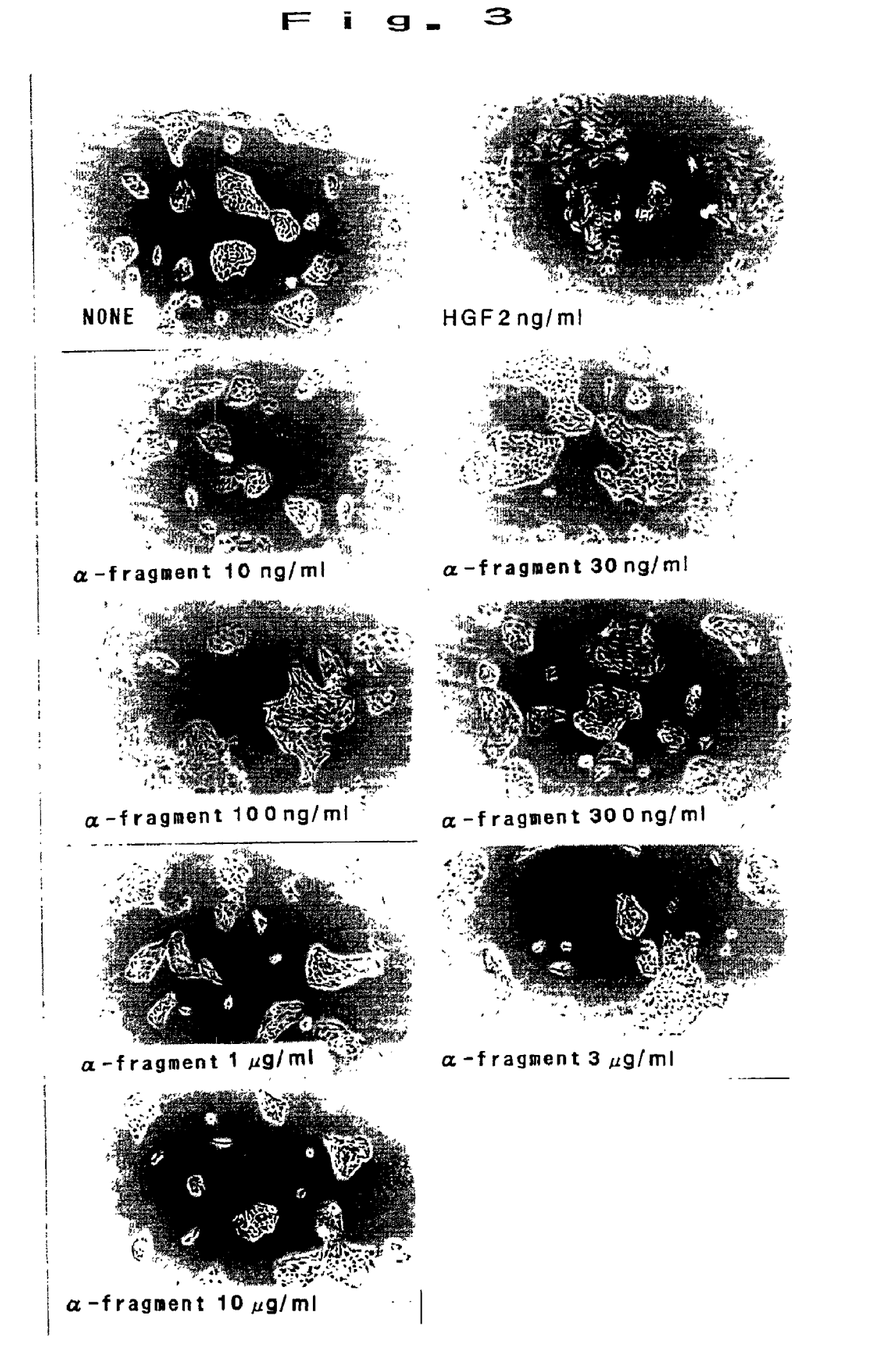
FIG. 3 is a photograph showing the scattering effect of α-fragment on MDCK cells.
Figure 4:
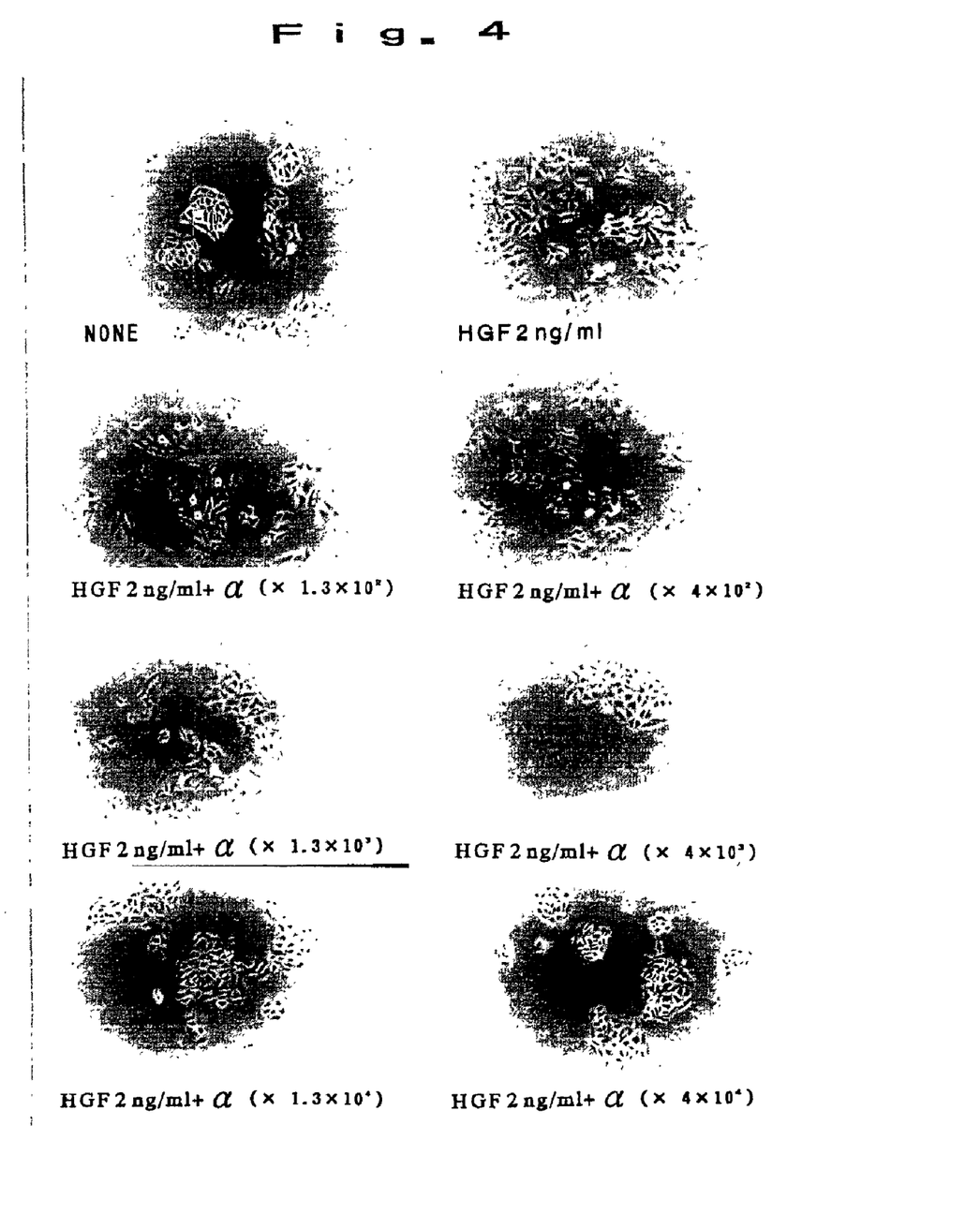
FIG. 4 is a photograph showing the scattering effect of α-fragment on MDCK cells in coexistence of HGF.

MDCK cells were prepared in $2 \times 10^4$ cells/ml in 10% FBS added DMEM culture medium, and seeded in 48 well plates at 250 ml/well. By adding α-fragment alone in a range of 10 ng/ml to 10 mg/ml and cultivating for 24 hours, the surface was observed by a phase-contrast microscope. Results are shown in FIG. 3. As shown in FIG. 3, scattering action was not recognized in α-fragment. In succession, adding simultaneously with 2 ng/ml of HGF, the inhibitory effect on HGF was studied. Results are shown in FIG. 4 (in the photograph, the indication of "α" denotes the concentration of α-fragment (magnification), same hereinafter). As shown in FIG. 4, when exceeding the concentration of 1000 times, inhibition of scattering was observed dose-dependently. Thus, α-fragment was strongly suggested to be an antagonist of HGF.

Example 3
Analysis of Action as Mitogen using Rat Liver Cells

Figure 5:
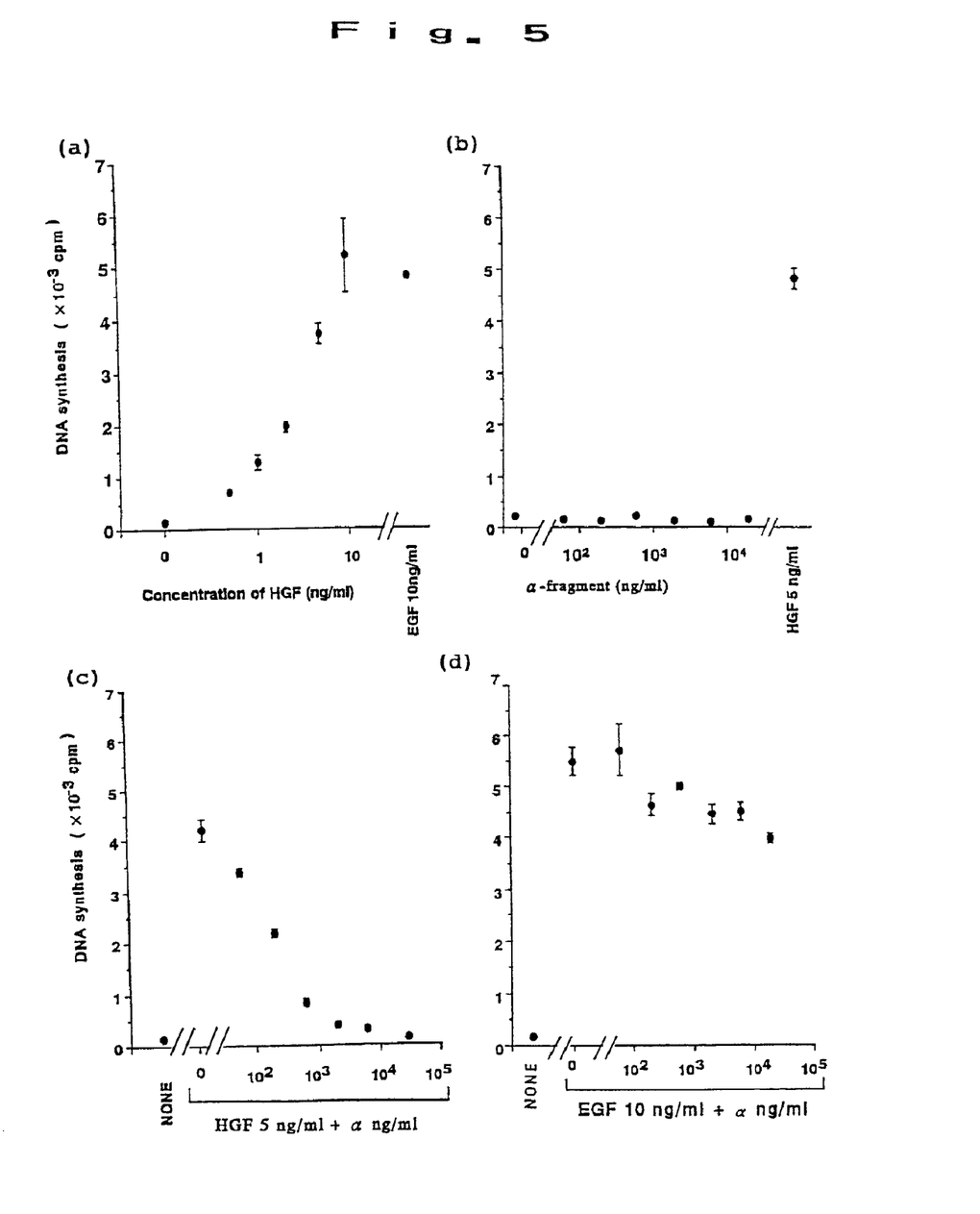
FIG. 5 is a graph showing the effects of HGF, EGF and α-fragment on DNA synthesis of rat liver cells. In the graph, (a) is a system by adding HGF, (b) is a system by adding α-fragment, (c) is a system by adding α-fragment in coexistence of 5 ng/ml of HGF, and (d) is a system by adding α-fragment in coexistence of 10 ng/ml of EGF.

Rat liver cells were cultivated on 38 well plates so as to occupy an area of about 50%, and HGF, EGF and α-fragment were added, and cultivated for 22 hours. By labeling with $^{125}$I-BrdU (0.15 mCi/well) for 4 hours, the activity was measured by scintillation counter. Results are shown in FIG. 5. In a range of $10^2$ ng/ml to $10^4$ ng/ml of α-fragment, the DNA synthesis promoting action was not recognized. When added simultaneously with 5 ng/ml of HGF, it was known that the mitogen activity of HGF was suppressed dose-dependently (see FIG. 5c). Hence, α-fragment was proved to be an antagonist to mitogen and motogen activity of HGF.

Example 4
Action of α-fragment on Invasion of Cancer Cells Induced by HGF

Figure 6:
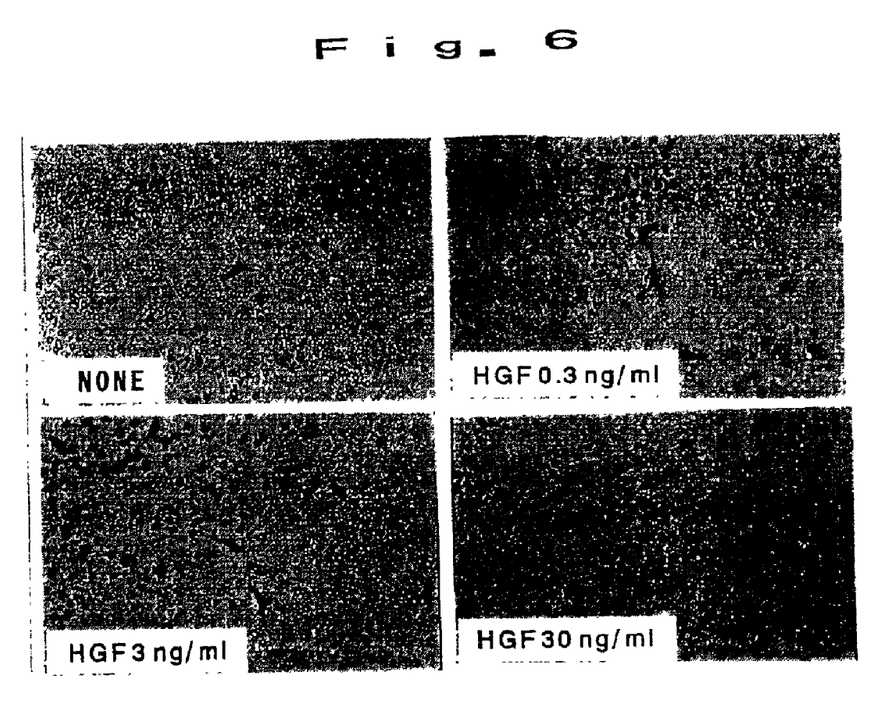
FIG. 6 is a, photograph showing the effect of α-fragment on invasion of GB-d1 cells.
Figure 7:
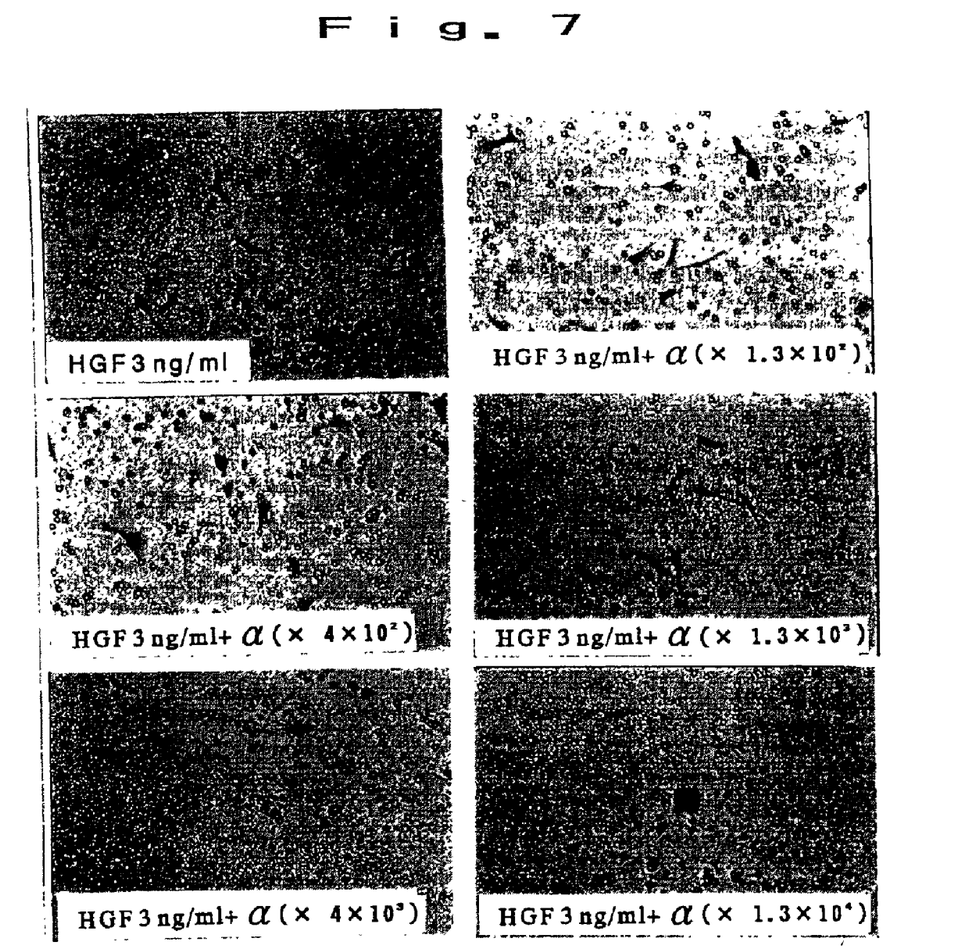
FIG. 7 is at photograph showing the effect of α-fragment on invasion of GB-d1 cells in coexistence of HGF.
Figure 8:
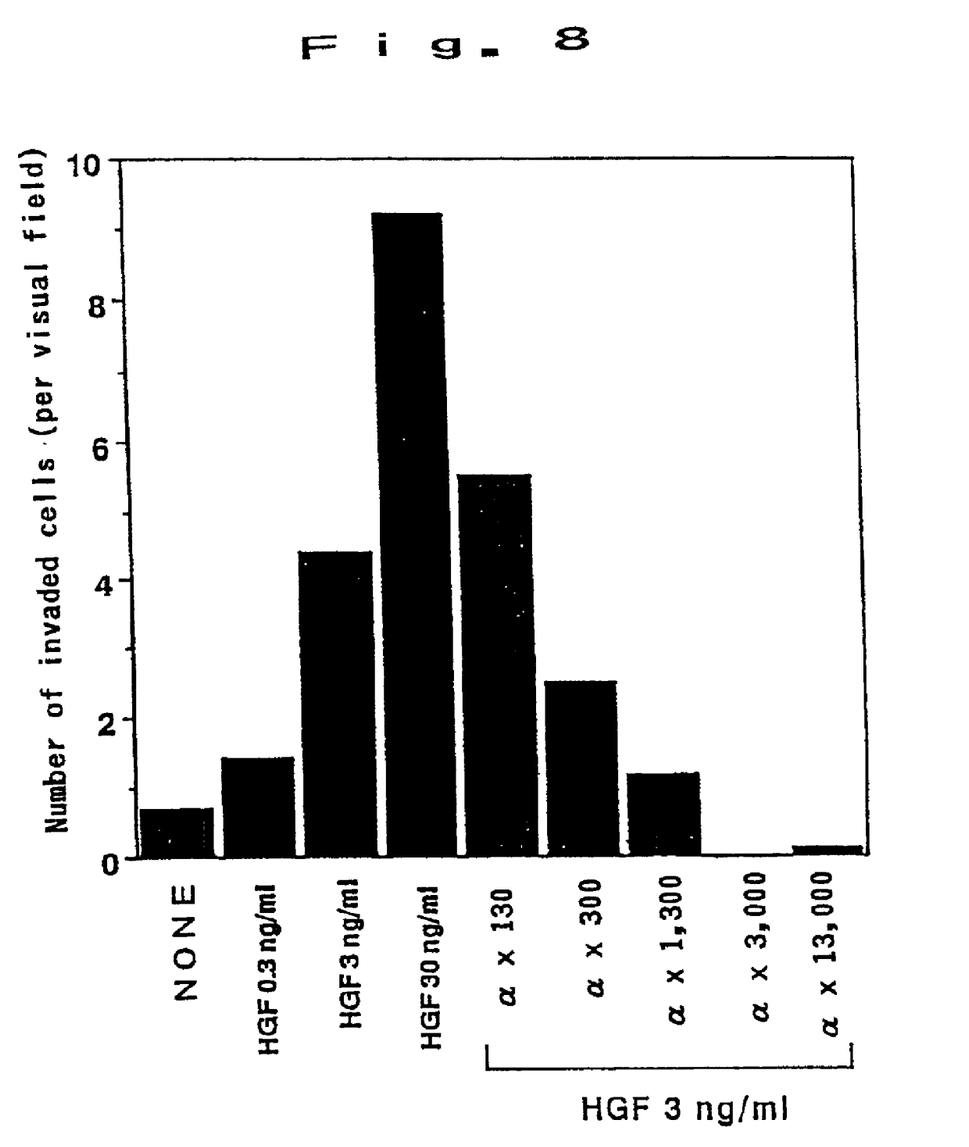
FIG. 8 is a graphic expression of results of FIG. 6 and FIG. 7.

In the basal film invasion model using quantitative Matrigen invasion chamber (24 wells), the effect of α-fragment on the cancer cell invasion inducing action of HGF was studied. Adjusting GB-d1 cells to $1.5 \times 10^4$ cells/200 ml/well, cells were seeded in the upper chamber. In 500 ml of culture medium of lower chamber, 2 ng/ml of HGF and α-fragment were added, and cultivated for 24 hours, and stained by H&E after fixing. Microscopically, ten arbitrary fields (8.4 mm$^2$) were observed, and the ability of invasion was evaluated by the number of cells invading into the lower surface of the filter. As a result, HGF promoted invasion of GB-d1 cells dose-dependently (see FIG. 6). The action of α-fragment on 3 ng/ml of HGF was studied, and α-fragment inhibited the action of HGF dose-dependently, that is, 130 times, 400 times, 4000 times, 13000 times of 3 ng/ml of HGF (see FIG. 7). Results of FIG. 6 and FIG. 7 are graphically expressed in FIG. 8.

It is known from these results that α-fragment is effective for suppressing invasion of cancer cells induced by HGF.

Preparation Example 1

A solution containing 1 mg of α-fragment, 1 g of mannitol and 10 mg of polysorbate 80 in 100 ml of physiological saline was aseptically prepared, and poured into 1 ml vials, and freeze-dried and sealed, and freeze-dry preparations were obtained.

Preparation Example 2

An aqueous solution containing 1 mg of α-fragment and 100 mg of human serum albumin in 100 ml of 0.02M phosphate buffer solution (containing 0.15M NaCl and 0.01% polysorbate 80, pH 7.4) was aseptically prepared, and poured into 1 ml vials, and freeze-dried and sealed, and freeze-dry preparations were obtained.

Preparation Example 3

A solution containing 1 mg of α-fragment, 2 g of sorbitol, 2 g of glycine and 10 mg of polysorbate 80 in 100 ml of distilled water for injection was aseptically prepared, and poured into 1 ml vials, and freeze-dried and sealed, and freeze-dry preparations were obtained.

What is claimed is:

1. A pharmaceutical composition comprising an isolated and purified protein, which consists of an amino acid sequence of SEQ ID NO: 1 and a pharmaceutically acceptable excipient.

2. An anti-cancer agent comprising isolated and purified protein, which consists of an amino acid sequence of SEQ ID NO: 1.

3. An invasion suppressant or metastasis suppressant of cancer cells comprising an isolated and purified protein, which consists of an amino acid sequence of SEQ ID NO: 1.

4. A method of inhibiting metastasis comprising administering to an individual in need thereof a pharmaceutically acceptable amount of a protein, which consists of SEQ ID NO: 1.

5. An isolated and purified protein consisting of an amino acid sequence of SEQ ID NO: 1.

* * * * *

SEQUENCE LISTING

<160> NUMBER OF SEQ ID NOS: 1

<210> SEQ ID NO 1
<211> LENGTH: 447
<212> TYPE: PRT
<213> ORGANISM: Homo sapiens

<400> SEQUENCE: 1

```
Gln Arg Lys Arg Arg Asn Thr Ile His Glu Phe Lys Lys Ser Ala Lys
1               5                   10                  15

Thr Thr Leu Ile Lys Ile Asp Pro Ala Leu Lys Ile Lys Thr Lys Lys
            20                  25                  30

Val Asn Thr Ala Asp Gln Cys Ala Asn Arg Cys Thr Arg Asn Lys Gly
        35                  40                  45

Leu Pro Phe Thr Cys Lys Ala Phe Val Phe Asp Lys Ala Arg Lys Gln
    50                  55                  60

Cys Leu Trp Phe Pro Phe Asn Ser Met Ser Ser Gly Val Lys Lys Glu
65                  70                  75                  80

Phe Gly His Glu Phe Asp Leu Tyr Glu Asn Lys Asp Tyr Ile Arg Asn
                85                  90                  95

Cys Ile Ile Gly Lys Gly Arg Ser Tyr Lys Gly Thr Val Ser Ile Thr
            100                 105                 110

Lys Ser Gly Ile Lys Cys Gln Pro Trp Ser Ser Met Ile Pro His Glu
        115                 120                 125

His Ser Phe Leu Pro Ser Ser Tyr Arg Gly Lys Asp Leu Gln Glu Asn
    130                 135                 140

Tyr Cys Arg Asn Pro Arg Gly Glu Glu Gly Gly Pro Trp Cys Phe Thr
145                 150                 155                 160

Ser Asn Pro Glu Val Arg Tyr Glu Val Cys Asp Ile Pro Gln Cys Ser
                165                 170                 175

Glu Val Glu Cys Met Thr Cys Asn Gly Glu Ser Tyr Arg Gly Leu Met
            180                 185                 190

Asp His Thr Glu Ser Gly Lys Ile Cys Gln Arg Trp Asp His Gln Thr
        195                 200                 205

Pro His Arg His Lys Phe Leu Pro Glu Arg Tyr Pro Asp Lys Gly Phe
    210                 215                 220

Asp Asp Asn Tyr Cys Arg Asn Pro Asp Gly Gln Pro Arg Pro Trp Cys
225                 230                 235                 240

Tyr Thr Leu Asp Pro His Thr Arg Trp Glu Tyr Cys Ala Ile Lys Thr
                245                 250                 255

Cys Ala Asp Asn Thr Met Asn Asp Thr Asp Val Pro Leu Glu Thr Thr
            260                 265                 270

Glu Cys Ile Gln Gly Gln Gly Glu Gly Tyr Arg Gly Thr Val Asn Thr
        275                 280                 285

Ile Trp Asn Gly Ile Pro Cys Gln Arg Trp Asp Ser Gln Tyr Pro His
    290                 295                 300

Glu His Asp Met Thr Pro Glu Asn Phe Lys Cys Lys Asp Leu Arg Glu
305                 310                 315                 320

Asn Tyr Cys Arg Asn Pro Asp Gly Ser Glu Ser Pro Trp Cys Phe Thr
                325                 330                 335

Thr Asp Pro Asn Ile Arg Val Gly Tyr Cys Ser Gln Ile Pro Asn Cys
            340                 345                 350

Asp Met Ser His Gly Gln Asp Cys Tyr Arg Gly Asn Gly Lys Asn Tyr
```

-continued

```
            355                 360                 365
Met Gly Asn Leu Ser Gln Thr Arg Ser Gly Leu Thr Cys Ser Met Trp
    370                 375                 380

Asp Lys Asn Met Glu Asp Leu His Arg His Ile Phe Trp Glu Pro Asp
385                 390                 395                 400

Ala Ser Lys Leu Asn Glu Asn Tyr Cys Arg Asn Pro Asp Asp Asp Ala
            405                 410                 415

His Gly Pro Trp Cys Tyr Thr Gly Asn Pro Leu Ile Pro Trp Asp Tyr
            420                 425                 430

Cys Pro Ile Ser Arg Cys Glu Gly Asp Thr Thr Pro Thr Ile Val
            435                 440                 445
```